United States Patent
Cui et al.

(10) Patent No.: US 11,439,300 B2
(45) Date of Patent: Sep. 13, 2022

(54) BINOCULAR BRIGHTNESS SENSITIVITY MEASUREMENT METHOD BASED ON WEARABLE DISPLAY DEVICE, DEVICE AND MOBILE TERMINAL

(71) Applicant: CLOUDMINDS (SHENZHEN) ROBOTICS SYSTEMS CO., LTD., Guangdong (CN)

(72) Inventors: Huakun Cui, Guangdong (CN); Kai Wang, Guangdong (CN); Shiguo Lian, Guangdong (CN); Guanghua Yang, Guangdong (CN)

(73) Assignee: CLOUDMINDS ROBOTICS CO., LTD., Shanghai (CN)

( * ) Notice: Subject to any disclaimer, the term of this patent is extended or adjusted under 35 U.S.C. 154(b) by 261 days.

(21) Appl. No.: 16/808,766

(22) Filed: Mar. 4, 2020

(65) Prior Publication Data

US 2020/0196855 A1 Jun. 25, 2020

Related U.S. Application Data (63) Continuation of application No. PCT/CN2017/100414, filed on Sep. 4, 2017.

(51) Int. Cl.
| | | |
|---|---|---|
| *A61B 3/06* | (2006.01) | |
| *A61B 3/08* | (2006.01) | |
| *G16H 40/67* | (2018.01) | |
| *G16H 40/63* | (2018.01) | |
| *G16H 70/20* | (2018.01) | |

(Continued)

(52) U.S. Cl.
CPC .............. *A61B 3/063* (2013.01); *A61B 3/005* (2013.01); *A61B 3/08* (2013.01); *G06T 7/0014* (2013.01); *G06T 19/20* (2013.01); *G16H 40/63* (2018.01); *G16H 40/67* (2018.01); *G16H 70/20* (2018.01);

(Continued)

(58) Field of Classification Search
None
See application file for complete search history.

(56) References Cited

U.S. PATENT DOCUMENTS

| 6,911,916 B1 * | 6/2005 | Wang ..................... A61B 17/00 340/3.7 |
|---|---|---|
| 10,055,887 B1 * | 8/2018 | Gil .......................... G02B 27/017 |
| 2012/0069038 A1 * | 3/2012 | Suen ..................... H04N 13/133 345/589 |

FOREIGN PATENT DOCUMENTS

| CN | 101292928 A | 10/2008 |
|---|---|---|
| CN | 102461192 A | 5/2012 |

(Continued)

OTHER PUBLICATIONS

International Search Report dated May 30, 2018; PCT/CN2017/100414.

(Continued)

*Primary Examiner* — Kyle Zhai (57) ABSTRACT

A binocular brightness sensitivity measurement method based on a wearable display device includes: loading a first test image and a second test image which has a brightness different from that of the first test image respectively for two eyes of a user under test; adjusting the brightness of the first test image and/or the second test image until a predefined brightness sensitivity perception test condition is fulfilled; acquiring a brightness difference between the first test image and the second test image; and determining a binocular brightness sensitivity of the user under test based on the brightness difference.

15 Claims, 5 Drawing Sheets

(51) Int. Cl.
  *A61B 3/00* (2006.01)
  *G06T 7/00* (2017.01)
  *G06T 19/20* (2011.01)
  *H04L 67/1097* (2022.01)
(52) U.S. Cl.
  CPC ...... *H04L 67/1097* (2013.01); *G06T 2210/41* (2013.01)

(56) References Cited

FOREIGN PATENT DOCUMENTS

| | | | |
|---|---|---|---|
| CN | 103876886 A | * | 6/2014 |
| CN | 103876886 A | | 6/2014 |
| CN | 104382552 A | | 3/2015 |
| CN | 107095733 A | | 8/2017 |
| WO | 8704264 A1 | | 7/1987 |

OTHER PUBLICATIONS

1st Office Search Report dated Apr. 12, 2019 by the CN Office; Appln.No.2017800025975.

\* cited by examiner

BINOCULAR BRIGHTNESS SENSITIVITY MEASUREMENT METHOD BASED ON WEARABLE DISPLAY DEVICE, DEVICE AND MOBILE TERMINAL

CROSS-REFERENCE TO RELATED APPLICATIONS

This application is a continuation of International Application No. PCT/CN2017/100414 with an international filing date of Sep. 4, 2017, the entire contents of which are incorporated herein by reference.

TECHNICAL FIELD

The present application relates to the technical field of virtual reality, and in particular, relates to a binocular brightness sensitivity measurement method based on a wearable display device, a device and a mobile terminal.

BACKGROUND

With the development of network technologies and machine vision and image recognition technologies, more and more wearable display devices are perceived by pleasant by users. For example, immersive virtual reality devices, augmented reality devices or even mobile terminals may be equipped with a wearable bracket to provide a realistic virtual environment and interaction environment for the users.

Where the wearable display device provides the real virtual environment and convenient interaction environment, more and more online interaction applications gain development, for example, online diagnosis and treatment or online meeting or the like.

Based on the human eye mechanism and human vision model, the brightness subjectively perceived by the human eyes is not absolutely the same as the actual brightness, but a corresponding relationship is present therebetween. The human eyes may perceive an extremely wide brightness range, from thousands of a nit to millions of nits. In different brightness environments, the human eyes perceive different relative brightness feelings for the same actual brightness. For example, with respect to the same lamp, the relative brightness feelings for the human eyes in the daytime are different from those in the nighttime. In addition, when the human eyes are quite adaptive to an environment brightness, the perceivable range may become smaller. Amblyopia, keratitis, ametropia, cataract, vitreous opacity, retinopathy and maculopathy and the like ophthalmic diseases may cause different perception capabilities against the brightness for two eyes of a patient, and thus affect normal life of the patient. How to accurately measure the perception capabilities against the brightness of the left and right eyes exerts a great significance for treatment of the above ophthalmic diseases.

However, in the prior art, the binocular brightness sensitivity is measured by using very large equipment, users need to go to the hospital for diagnosis before taking measurements. Or, the brightness sensitivity is measured by using a polarization-type three-dimensional television. The above measurement equipment cannot be moved arbitrarily, and there is a measurement error in the measurement results due to the position error and environmental interference of the measured user.

Therefore, the traditional binocular brightness sensitivity detection technology needs to be improved.

SUMMARY

An embodiment of the present application provides a binocular brightness sensitivity measurement method based on a wearable display device. The method includes: loading a first test image and a second test image which has a brightness different from that of the first test image respectively for two eyes of a user under test; adjusting the brightness of the first test image and/or the second test image until a predefined brightness sensitivity perception test condition is fulfilled; acquiring a brightness difference between the first test image and the second test image; and determining a binocular brightness sensitivity of the user under test based on the brightness difference.

Another embodiment of the present application provides a wearable display device for measuring a binocular brightness sensitivity. The wearable display device includes: a first three-dimensional display unit and a second three-dimensional display unit; wherein the wearable display device further includes a brightness adjusting module, an acquiring module and a determining module; wherein with respect to two eyes of a user under test, the first three-dimensional display unit is configured to load a first test image, and the second three-dimensional display unit is configured to load a second test image which has a brightness different from that of the first test image; the brightness adjusting module is configured to adjust the brightness of the first test image and/or the second test image until a predefined brightness sensitivity perception test condition is fulfilled; the acquiring module is configured to acquire a brightness difference between the first test image and the second test image; and the determining module is configured to determine a binocular brightness sensitivity of the user under test based on the brightness difference.

Still another embodiment of the present application provides a mobile terminal for measuring a binocular brightness sensitivity. The mobile terminal includes: a head-mounted bracket, a first three-dimensional display unit and a second three-dimensional display unit; wherein the wearable display device further includes a brightness adjusting module, an acquiring module and a determining module; wherein with respect to two eyes of a user under test, the first three-dimensional display unit is configured to load a first test image, and the second three-dimensional display unit is configured to load a second test image which has a brightness different from that of the first test image; the brightness adjusting module is configured to adjust the brightness of the first test image and/or the second test image until a predefined brightness sensitivity perception test condition is fulfilled; the acquiring module is configured to acquire a brightness difference between the first test image and the second test image; and the determining module is configured to determine a binocular brightness sensitivity of the user under test based on the brightness difference.

BRIEF DESCRIPTION OF THE DRAWINGS

One or more embodiments are illustrated by way of example, and not by limitation, in the figures of the accompanying drawings, wherein components having the same reference numeral designations represent like components throughout. The drawings are not to scale, unless otherwise disclosed.

DETAILED DESCRIPTION

For clearer descriptions of the objectives, technical solutions, and advantages of the present application, the present application is further described with reference to specific embodiments and attached drawings. It should be understood that the specific embodiments described herein are only intended to explain the present application instead of limiting the present application.

Figure 1:
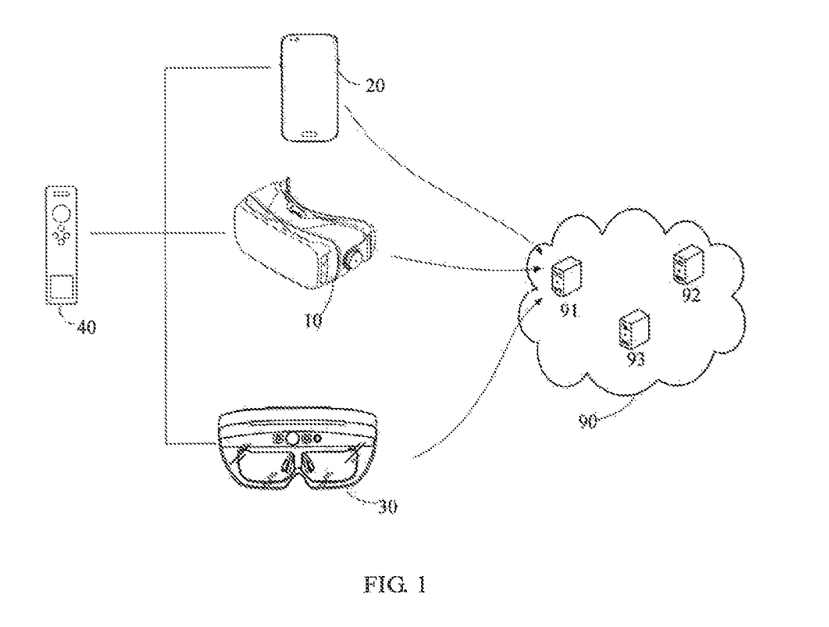
FIG. 1 is a frame diagram of a binocular brightness sensitivity measurement system based on a wearable display device according to an embodiment of the present application.

Referring to FIG. 1, a binocular brightness sensitivity measurement system based on a wearable display device according to an embodiment of the present application includes at least one pair of wearable display devices, an interaction end and a cloud end 90. The wearable display device may be a virtual reality (VR) device 10. The wearable display device may also be an augmented reality (AR) device 30. The wearable display device may also be a mobile terminal 20. Each of the above exemplified wearable display devices may be wirelessly connected to an interaction end 40 and meanwhile connected to a cloud end 90. The cloud end 90 is constructed by networking of a plurality of cloud servers 91 to 93.

The virtual reality device employs virtual reality and is a computer system that is capable of creating and providing a virtual three-dimensional world. The virtual reality device creates a three-dimensional virtual world reflecting in real time physical object changes and mutual interactions for users, and provides a vision for observing a virtual world and provides there-dimensional interactive operations for the user by auxiliary sensing equipment such as helmet displays, data gloves and the like, such that the user may directly participate in the interactive operations and explore changes and interactions of a simulated object in a virtual spatial environment. Therefore, the virtual reality technology is recognized as a revolution in the man-machine interface technology. The virtual reality technology is a fruit of the computer technology, the sensing technology, the man-machine interface technology, the artificial intelligence technology and the like high technologies. Verisimilitude and real-time interaction provide solid supports for the system simulation technology, and meanwhile provide immersion, interaction and imagination. An augmented reality (AR) device further includes glasses by which the real world may be observed. By means of the glasses and a projected virtual three-dimensional image, the user may observe the real world while seeing the virtual three-dimensional world.

The wearable display device in this technical solution mainly include: a high-performance operation and processing unit, a three-dimensional display unit and an interaction end 40. The three-dimensional display unit includes two independent sets of sub display units, that is, a first three-dimensional display unit and a second three-dimensional display unit. These two sets of sub display units display two independent test images to the left eye and the right eye of the user. The high-performance operation and processing unit is configured to carry out real-time operation processing for a three-dimensional test image, and the interaction end 40 is configured to process input information of a user under test during the test process.

The detection fashions are categorized into static detection and dynamic detection with respect to different test images. The static detection refers to allowing the left eye and the right eye of the user under test to respectively observe two static test images, wherein positions of the objects in the one image are different from those of the objects in the other image, and display brightness of the two images is constantly adjusted. When the left eye and the right eye of the user under test perceives that the two images have the same brightness, an actual brightness difference between the two images may represent a binocular brightness sensitivity of the user under test.

The dynamic detection refers to allowing the left eye and the right eye of the user under test to observe dynamic test images. The brightness of the dynamic image is adjusted by the interaction end. When the objects in the dynamic test images move in a plane parallel to the two eyes of the user under test, an actual brightness difference between the two images may represent a binocular brightness sensitivity of the user under test.

The dynamic detection observes a principle based on the Pulfrich effect. The Pulfrich effect is an optimal illusion produced based on the fact that brain's perception on dark stimulations lags behind brain's perception on bright stimulations. The Pulfrich phenomenon means that when a pendulum is hung with a rope and is swung reciprocatively in a plane, if one eye is interrupted by a brown mirror, the trajectory of the pendulum observed by two eyes may transform from movement in a plane to three-dimensional movement with an elliptical trajectory. The Pulfrich effect is exerted because the eye observing a darker image transmits the image to the brain at a lower speed, and thus the brain constructs a spatial depth that is not practically existent based on such a vision error. When a pendulum is swung from the left to the right in a plane parallel to two eyes, if a neutral filter is arranged in front of the right eye, retinal illumination may be lowered and thus information transmission by the right eye is slowed. When a pendulum is swung from the left to the right, the position of the pendulum observed by the right eye is behind the position of the pendulum observed by the left eye such that a crossed disparity is observed by the two eyes, and thus the pendulum is seemed to be closer. When a pendulum is swung from the right to the left, on the contrary, an uncrossed disparity is observed, and thus the pendulum is seemed to be farther. As such, it is observed that the pendulum is swung along a three-dimensional elliptical trajectory, which is caused by a time parallax. In clinics, the Pulfrich effect may be employed to measure a degree of transmission retardance due to optic nerves. That is, a neural filter is arranged in front of a normal eye, and the density of the filter is gradually increased until the Pulfrich phenomenon disappears.

In the dynamic detection, if two eyes of the user under test have different brightness sensitivities, the user under test may perceive that the objects in the dynamic test images are not moving in a plane. During the process of adjusting the brightness of the dynamic test images, when the user under test perceives that the objects in the dynamic test images move in the same plane, an actual brightness difference between the two dynamic test images may represent a binocular brightness sensitivity of the user under test.

Embodiment 1

This embodiment relates to a wearable display device for measuring a binocular brightness sensitivity.

The wearable display device displays a test image in a first three-dimensional display unit and a second three-dimensional display unit. A user under test wears the wearable helmet, observes the test image in the first three-dimensional display unit and the second three-dimensional display unit with the left eye and the right eye respectively, makes a brightness adjustment based on the observed test image, and finally determines a brightness sensing capability difference between the left eye and the right eye, that is, a binocular brightness sensitivity of the user under test.

Figure 2:
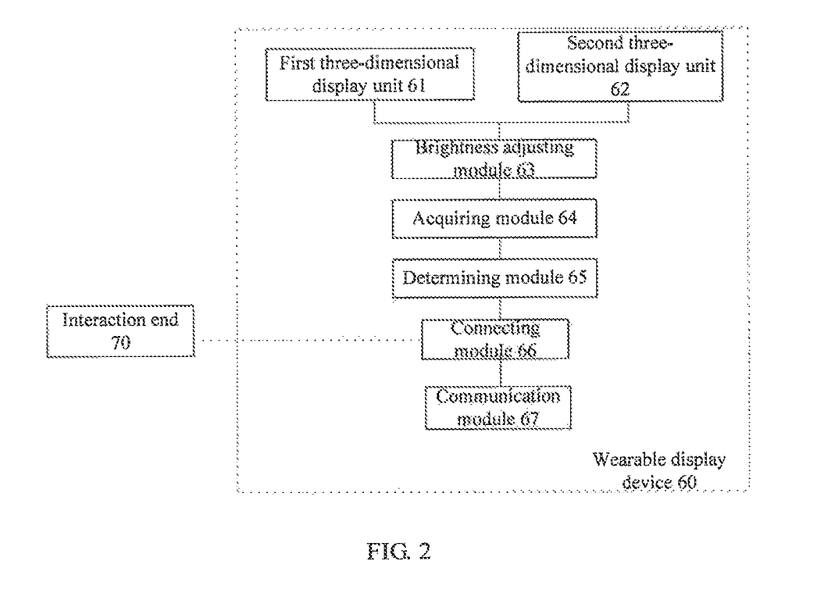
FIG. 2 is a module diagram of a wearable display device for measuring a binocular brightness sensitivity according to an embodiment of the present application.

Referring to FIG. 2, the wearable display device 60 includes a first three-dimensional display unit 61, a second three-dimensional display unit 62, a brightness adjusting module 63, an acquiring module 64, a determining module 65 and a connecting module 66.

With respect to two eyes of a user under test, the first three-dimensional display unit 61 loads a first test image, and the second three-dimensional display unit 62 loads a second test image which has a brightness different from that of the first test image.

The connecting module 66 is wirelessly connected to the interaction end 40, and the interaction end 40 collects an interaction instruction from the user under test, and wirelessly sends the interaction instruction to the connecting module 66.

The brightness adjusting module 63 adjusts the brightness of the first test image and/or the second test image based on the interaction instruction until a predefined brightness sensitivity perception test condition is fulfilled. In this case, the acquiring module 64 acquires a brightness difference between the first test image and the second test image. The determining module 65 determines a binocular brightness sensitivity of the user under test based on the brightness difference.

A specific test process is introduced as follows:

When the user under test wears the virtual reality device 10 or the augmented reality device 30 or the like hardware device, a corresponding device software system selects or makes two images each having a different brightness, i.e., the first test image and the second test image, and then displays the first test image and the second test image on display windows of the first three-dimensional display unit and the second three-dimensional display unit respectively.

Corresponding to the dynamic detection and the static detection, in the static detection, the first test image and the second test image are static images, and in the dynamic detection, the first test image and the second test image are dynamic images.

In an embodiment illustrating the static detection, the first test image is a first static image, and the second test image is a second static image.

Figure 6:
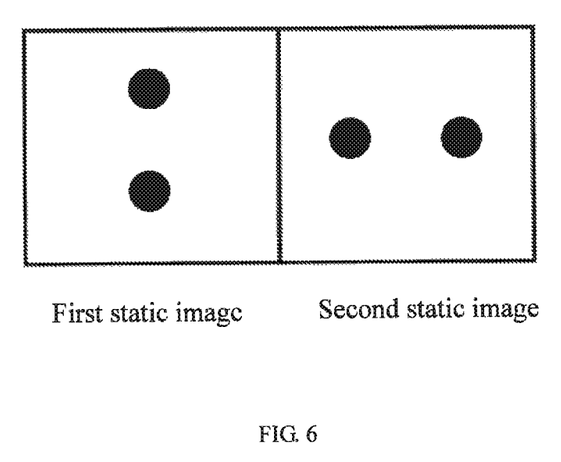
FIG. 6 is a flowchart of a binocular brightness sensitivity measurement method with respect to a first static image and a second static image included in the static image according to an embodiment of the present application.
Figure 7:
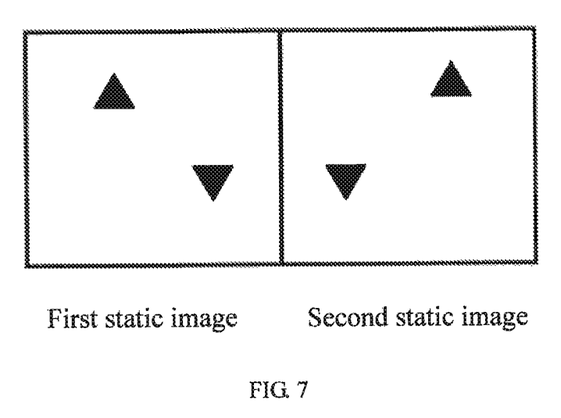
FIG. 7 is another flowchart of a binocular brightness sensitivity measurement method with respect to a first static image and a second static image included in the static image according to an embodiment of the present application.

Referring to FIG. 6 and FIG. 7, an embodiment of the first static image and the second static image is illustrated. The number of objects, and shapes and colors thereof in the first static image are not necessarily the same as those in the second static image, which are not necessarily in a vertical arrangement or a horizontal arrangement. FIG. 6 and FIG. 7 illustrate several examples. In practice, implementation of the first static image and the second static image is not limited hereto. Image elements in the first static image or the second static image have the same brightness, whereas the brightness of the first static image is different from that of the second static image. The number of objects, and positions and shapes of the objects in the first static image are different from those in the second static image. All the objects in the first static image or in the second static image have the same brightness, whereas the objects in the first static image have a brightness different from that of the objects in the second static image.

The brightness perception test condition is that the user perceives that the first static image and the second static image have the same brightness.

When the interaction instruction is an interaction instruction for improving the brightness of the first static image, the brightness adjusting module 63 increases the brightness of the first static image, and decreases the brightness of the second static image. When the interaction instruction is an interaction instruction for improving the brightness of the second static image, the brightness adjusting module 63 increases the brightness of the second static image, and decreases the brightness of the first static image.

When the user under test observes that the objects in the first static image and the second static image have the same brightness, the user under test issues a stop instruction, and the determining module 65 calculates a brightness difference between the first static image and the second static image, locally stores data of the brightness difference, and determines a binocular brightness sensitivity of the user under test based on the brightness difference. In other embodiments, the determined binocular brightness sensitivity of the user under test may also be transmitted to the cloud end 90 via a communication module, or transmitted to a mobile terminal for browsing.

After the user under test wears the wearable display device, the user firstly observes the first static image and the second static image on two display windows targeted by two eyes of the user, and then adjusts the brightness of each individual display window based on an interaction instruction input by the interaction end. When the user under test considers that the first static image and the second static image have the same brightness, a brightness difference between the left display window and the right display window is a brightness perception capability difference between the left eye and the right eye. In this way, based on a stored mapping table, a binocular brightness sensitivity value may be obtained.

In an embodiment illustrating the dynamic detection, the first test image is a first dynamic image, and the second test image is a second dynamic image.

Dynamic objects in the first dynamic image and the second dynamic image reciprocate in a plane parallel to two eyes of the user directly in front of the user under test, and the dynamic objects in the first dynamic image and the second dynamic image have the same positions and movement trajectories. The dynamic object in the first dynamic image has a brightness different from that of the dynamic object in the second dynamic image.

In the embodiment illustrating the dynamic detection, the brightness perception test condition is that the movement trajectories of the dynamic objects observed by the user are in the same plane.

When the interaction instruction from the interaction end 40 is an interaction instruction for improving the brightness of the first dynamic image, the brightness adjusting module 63 increases the brightness of the first dynamic image, and decreases the brightness of the second dynamic image; and when the interaction instruction is an interaction instruction for improving the brightness of the second dynamic image, the brightness adjusting module 63 increases the brightness of the second dynamic image, and decreases the brightness of the first dynamic image.

For example, the dynamic object displayed on the left and right display windows of the first three-dimensional display unit and the second three-dimensional display unit is a pendulum, a fly or the like object. Hereinafter, description is given using the pendulum as an example, and the pendulum moves from the left to the right reciprocatively just in front of the user under test in a plane parallel to two eyes of the user. A plurality of stationary reference objects, for example, upright columns or the like for facilitating observation, are arranged respectively on two sides of the pendulum, a front side and a rear side. The dynamic object may apply different swing speed for the pendulum by the wearable display device, or change different background environments therefor.

Firstly, the brightness of the first dynamic image and the brightness of the second dynamic image on the wearable display device are adjusted to be consistent. If the user under test perceives that the moving object moves in an elliptical trajectory, the left eye and the right eye of the user under test have asymmetric brightness perception capabilities. Then, based on the elliptical trajectory observed by the user under test, an observation is made by means of top viewing about a central axis to determine whether the movement is clockwise or counterclockwise, and hence to modify a display brightness of each individual display window, until the user under test perceives that the trajectories of the dynamic objects are in the same plane. In this case, a brightness difference between the left display window and the right display window is a parameter for quantitatively assessing a binocular brightness sensitivity of the user under test.

When the user under test observes that the movement trajectories of the dynamic objects are in the same plane, a stop instruction is issued by the interaction end 40, the determining module 65 may calculate a brightness difference between the first dynamic image and the second dynamic image, and determines a binocular brightness sensitivity of the user under test based on the brightness difference, and locally stores the determined binocular brightness sensitivity. Alternatively, data of the measured binocular brightness sensitivity may also be transmitted to the cloud end 90 via a communication module, or transmitted to a mobile terminal for browsing.

The wearable display device 60 further includes a communication module 67, wherein the communication module 67 uploads the measured binocular brightness sensitivity to the cloud end 90, for example, a cloud server 91, based on a code of the user under test. The data of the measured binocular brightness sensitivity may be transmitted to the cloud end 90 via the communication module 67 for further analysis, or may be transmitted to the mobile terminal for browsing.

The wearable display device according to this embodiment may also be a mobile terminal 20 for measuring a binocular brightness sensitivity.

The mobile terminal 20 is mounted with a virtual reality system, and a first three-dimensional display unit and a second three-dimensional display unit are arranged in the virtual reality system. In the meantime, the mobile terminal 20 further includes a head-mounted bracket, wherein the head-mounted bracket includes a spacer layer. The mobile terminal 20 has a screen which is divided into a left display window and a right display window. After the mobile terminal 20 is mounted on the head-mounted bracket, the user may wear the mobile terminal 20 on the head, and observe independently the left display window and the right display window of the mobile terminal 20 under the effect of the spacer layer.

To measure the binocular brightness sensitivity, the mobile terminal 20 likewise includes a brightness adjusting module, an acquiring module and a determining module.

Functions and effects of the first three-dimensional display unit, the second three-dimensional display unit, the brightness adjusting module, the acquiring module and the determining module are the same as those of the above described wearable display device, which are thus not described herein any further.

The mobile terminal further includes a connecting module. The connecting module is wirelessly connected to the interaction end. The interaction end is configured to collect an interaction instruction for the user under test, and send the interaction instruction to the connecting module. When the interaction instruction is an interaction instruction for improving the brightness of the first dynamic image, the brightness adjusting module is further configured to improve the brightness of the first dynamic image, and decrease the brightness of the second dynamic image; and when the interaction instruction is an interaction instruction for improving the brightness of the second dynamic image, the brightness adjusting module is further configured to improve the brightness of the second dynamic image, and decrease the brightness of the first dynamic image.

Embodiment 2

This embodiment relates to a binocular brightness sensitivity measurement method based on a wearable display device.

Figure 3:
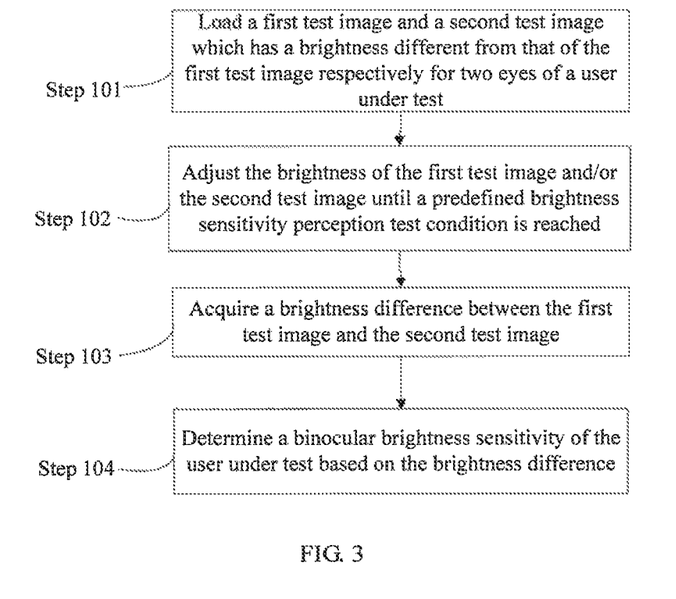
FIG. 3 is a main flowchart of a binocular brightness sensitivity measurement method according to an embodiment of the present application.

Referring to FIG. 3, from the perspective of measuring a binocular brightness sensitivity, the method mainly includes the following steps:

step 101: loading a first test image and a second test image which has a brightness different from that of the first test image respectively for two eyes of a user under test;

step 102: adjusting the brightness of the first test image and/or the second test image until a predefined brightness sensitivity perception test condition is reached;

step 103: acquiring a brightness difference between the first test image and the second test image; and step 104: determining a binocular brightness sensitivity of the user under test based on the brightness difference.

A specific test process is introduced as follows:

When the user under test wears the virtual reality device 10 or the augmented reality device 30 or the like hardware device, a corresponding device software system selects or makes two images each having a different brightness, i.e., the first test image and the second test image, and then displays the first test image and the second test image on display windows of the first three-dimensional display unit and the second three-dimensional display unit respectively.

Corresponding to the dynamic detection and the static detection, in the static detection, the first test image and the second test image are static images, and in the dynamic detection, the first test image and the second test image are dynamic images.

Figure 4:
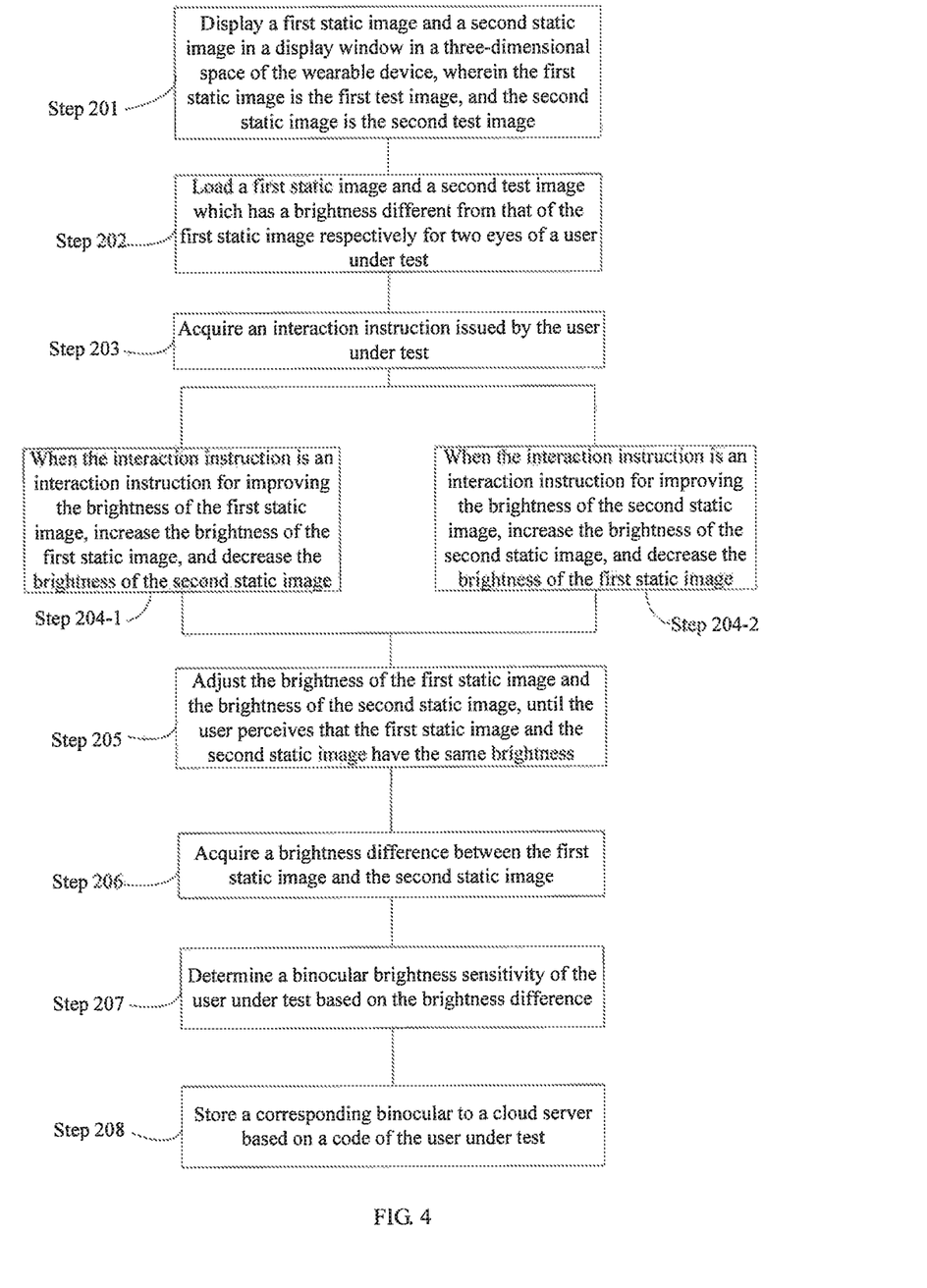
FIG. 4 is a flowchart of a binocular brightness sensitivity measurement method with respect to a static image according to an embodiment of the present application.

Referring to FIG. 4, a flowchart of a binocular brightness sensitivity measurement method with respect to a static image according an embodiment of the present application.

In an embodiment illustrating the static detection, the first test image is a first static image, and the second test image is a second static image. Image elements in the first static image or the second static image have the same brightness, whereas the brightness of the first static image is different from that of the second static image. The brightness perception test condition is that the user perceives that the first static image and the second static image have the same brightness.

The method includes the following steps:

step 201: displaying a first static image and a second static image in a display window in a three-dimensional space of the wearable display device, wherein the first static image is the first test image, and the second static image is the second test image;

step 202: loading a first static image and a second static image which has a brightness different from that of the first static image respectively for two eyes of a user under test;

step 203: acquiring an interaction instruction issued by the user under test, and adjusting the brightness of the first static image and the brightness of the second static image based on different interaction instructions;

step 204-1: when the interaction instruction is an interaction instruction for improving the brightness of the first static image, increasing the brightness of the first static image, and decreasing the brightness of the second static image;

step 204-2: when the interaction instruction is an interaction instruction or improving the brightness of the second static image, increasing the brightness of the second static image, and decreasing the brightness of the first static image;

step 205: adjusting the brightness of the first static image and the brightness of the second static image, until the user perceives that the first static image and the second static image have the same brightness;

step 206: acquiring a brightness difference between the first static image and the second static image;

step 207: determining a binocular brightness sensitivity of the user under test based on the brightness difference; and step 208: storing a corresponding binocular brightness sensitivity to a cloud server based on a code of the user under test.

Figure 5:
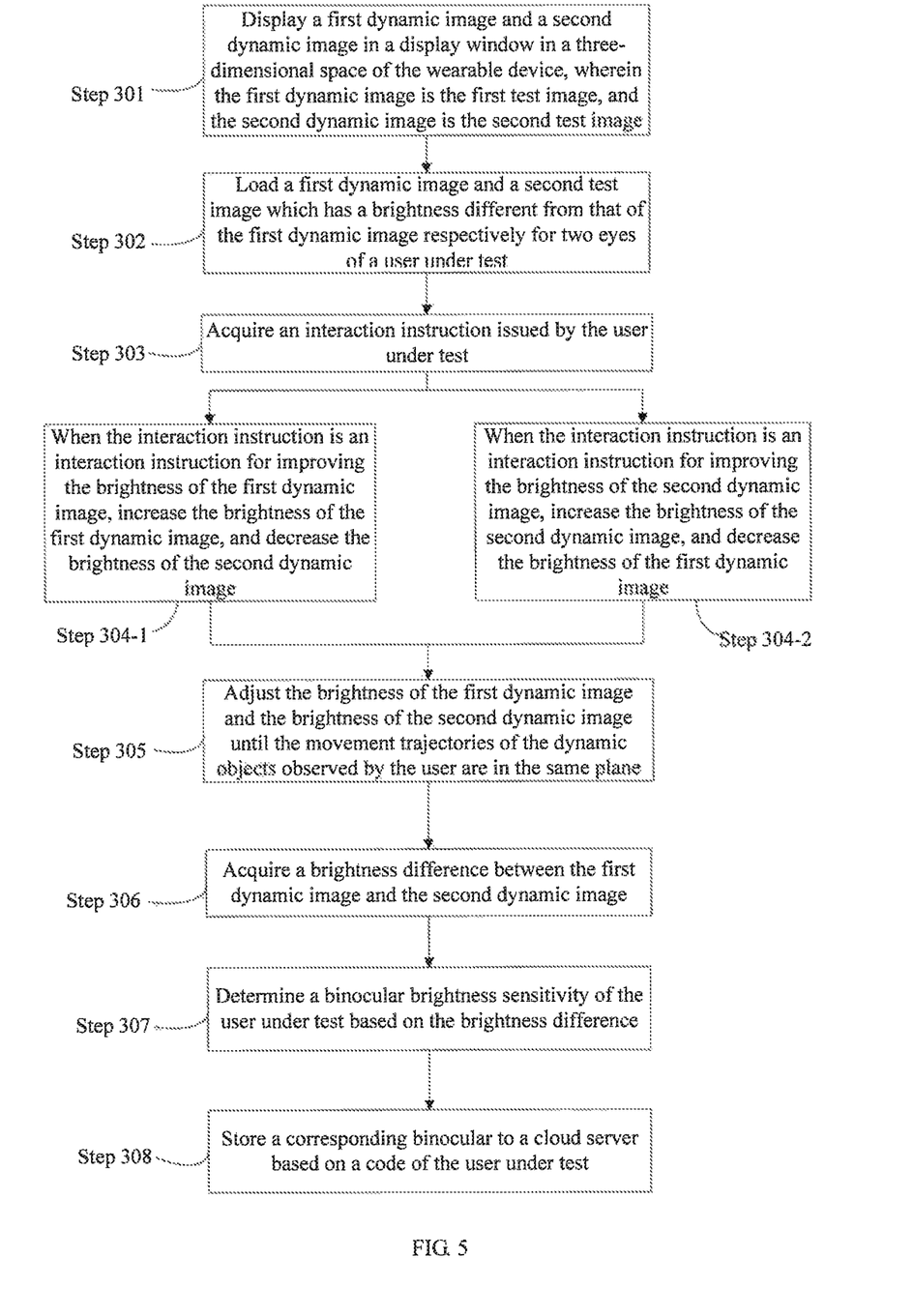
FIG. 5 is a flowchart of a binocular brightness sensitivity measurement method with respect to a dynamic image according to an embodiment of the present application.

Referring to FIG. 5, a flowchart of a binocular brightness sensitivity measurement method with respect to a dynamic image according to an embodiment of the present application.

In an embodiment illustrating the dynamic detection, the first test image is a first dynamic image, and the second test image is a second dynamic image; wherein dynamic objects in the first dynamic image and the second dynamic image reciprocate in a plane parallel to two eyes of the user directly in front of the user under test, the dynamic objects in the first dynamic image and the second dynamic image have the same positions and movement trajectories, the dynamic object in the first dynamic image has a brightness different from that of the dynamic object in the second dynamic image, and the brightness perception test condition is that the movement trajectories of the dynamic objects observed by the user are in the same plane.

The method includes the following steps:

step 301: displaying a first dynamic image and a second dynamic image in a display window in a three-dimensional space of the wearable display device, wherein the first dynamic image is the first test image, and the second dynamic image is the second test image;

step 302: loading a first dynamic image and a second dynamic image which has a brightness different from that of the first dynamic image respectively for two eyes of a user under test;

step 303: acquiring an interaction instruction issued by the user under test, and adjusting the brightness of the first dynamic image and the brightness of the second dynamic image based on different interaction instructions;

step 304-1: when the interaction instruction is an interaction instruction for improving the brightness of the first dynamic image, increasing the brightness of the first dynamic image, and decreasing the brightness of the second dynamic image;

step 304-2: when the interaction instruction is an interaction instruction for improving the brightness of the second dynamic image, increasing the brightness of the second dynamic image, and decreasing the brightness of the first dynamic image;

step 305: adjusting the brightness of the first dynamic image and the brightness of the second dynamic image until the movement trajectories of the dynamic objects observed by the user are in the same plane;

step 306: acquiring a brightness difference between the first dynamic image and the second dynamic image;

step 307: determining a binocular brightness sensitivity of the user under test based on the brightness difference; and step 308: storing a corresponding binocular brightness sensitivity to a cloud server based on a code of the user under test.

In conclusion, in the binocular brightness sensitivity measurement method based on a wearable display device, the device and mobile terminal according to the embodiments of the present application, in a three-dimensional space of the wearable display device, a first test image and a second test image which has a brightness that is different from that of the first test image are loaded respectively for two eyes of a user under test, and images are loaded to independent display units having no crosstalk, such that interference factors are reduced and measurement accuracy is improved. In addition, the user may conveniently adjust the brightness of the first test image and the brightness of the second test image until a predefined brightness sensitivity perception test condition is fulfilled, and therefore, the measurement is simple and the brightness sensitivity of the user under test is correctly reflected. In the binocular brightness sensitivity measurement method based on a wearable display device, the device and mobile terminal according to the embodiments of the present application, a pupillary distance, a focal length and display content of the wearable display device all may be adjusted, and the display content may be precisely controlled, for example, environmental illumination, placement distance, color, texture, movement trajectory and the like of the objects in experiments. As compared with the traditional natural environment, in the virtual environment, interference in the real environment may be adjusted and eliminated; and further a relative positional relationship between the user under test and the test device may be precisely controlled, such that measurement errors due to position errors and environment interferences are prevented. The wearable display device may sufficiently isolates the optical path systems of the left eye and the right eye, such that no crosstalk is produced therebetween. This improves measurement accuracy.

Embodiment 3

Figure 8:
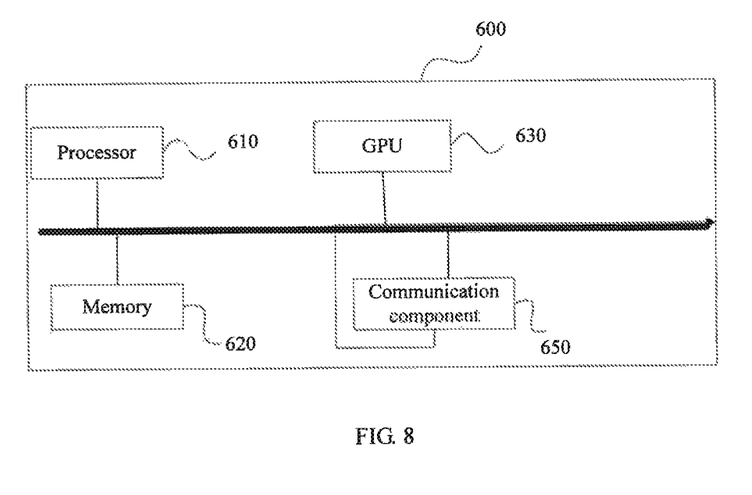
FIG. 8 is a frame diagram of hardware practicing the binocular brightness sensitivity measurement method according to an embodiment of the present application.

FIG. 8 is a schematic structural diagram illustrating hardware of an electronic device 600 for performing the binocular brightness sensitivity measurement method information according to an embodiment of the present application.

As illustrated in FIG. 8, the electronic device 600 includes at least one processor 610, a memory 620 and a communication component 650. FIG. 8 uses one processor 610 as an example. In an embodiment of a virtual reality wearable display device or an embodiment of an augmented reality wearable display device, the electronic device 600 may further include a graphics processing unit (GPU). The memory 620 stores instructions executable by the at least one processor 610. The instructions, when being executed by the at least one processor 610, may establish a data channel via the communication component 650, and cause the at least one processor 610 to perform the binocular brightness sensitivity measurement method.

The at least one processor 610, the memory 620 and the communication component 650 may be connected via a bus or in another manner, and FIG. 8 uses the bus as an example.

The memory 620, as a non-volatile computer readable storage medium, may be configured to store non-volatile software programs, and non-volatile computer-executable programs and modules, for example, the program instructions/modules corresponding to the binocular brightness sensitivity measurement methods according to the embodiments of the present application (for example, the first three-dimensional display unit 61, the second three-dimensional display unit 62, the brightness adjusting module 63, the acquiring module 64, the determining module 65 and the connecting module 66 as illustrated in FIG. 2). The non-volatile software programs, instructions and modules stored in the memory 620, when being run by the at least one processor 610, cause the processor 610 to perform various function applications and data processing of a wearable display device, that is, performing the binocular brightness sensitivity measurement methods in the above method embodiments.

The memory 620 may include a program memory area and data memory area, wherein the program memory area may store operation systems and application programs needed by at least function; and the data memory area may store data created according to the usage of the wearable display device. In addition, the memory 620 may include a high speed random access memory, or include a non-volatile memory, for example, at least one disk storage device, a flash memory device, or another non-volatile solid storage device. In some embodiments, the memory 620 optionally includes the memory remotely arranged relative to the processor 610, and such remote memory may be connected to the electronic device over the network. Examples of the above network include, but not limited to, the Internet, Intranet, local area network, mobile communication network and a combination thereof.

One or more modules are stored in the memory 620, which, when being executed by the at least one processor 610, perform the binocular brightness sensitivity measurement method according to any of the above method embodiments, for example, performing steps 101 to 104 in the method as illustrated in FIG. 3, steps 201 to 208 in the method as illustrated in FIG. 4 and steps 301 to 308 in the method as illustrated in FIG. 5; and implementing the functions of the first three-dimensional display unit 61, the second three-dimensional display unit 62, the brightness adjusting module 63, the acquiring module 64, the determining module 65 and the connecting module 66 as illustrated in FIG. 2.

The product may perform the method according to the embodiments of the present application, has corresponding function modules for performing the method, and achieves the corresponding beneficial effects. For technical details that are not illustrated in detail in this embodiment, reference may be made to the description of the methods according to the embodiments of the present application.

An embodiment of the present application provides a non-volatile computer-readable storage medium. The computer-readable storage medium stores computer-executable instructions, which, when being executed by at least one processor, cause the at least one processor to perform steps 101 to 104 in the method as illustrated in FIG. 3, steps 201 to 208 in the method as illustrated in FIG. 4 and steps 301 to 308 in the method as illustrated in FIG. 5; and implementing the functions of the first three-dimensional display unit 61, the second three-dimensional display unit 62, the brightness adjusting module 63, the acquiring module 64, the determining module 65 and the connecting module 66 as illustrated in FIG. 2.

The above described apparatus embodiments are merely for illustration purpose only. The units which are described as separate components may be physically separated or may be not physically separated, and the components which are illustrated as units may be or may not be physical units, that is, the components may be located in the same position or may be distributed into a plurality of network units. A part or all of the modules may be selected according to the actual needs to achieve the objectives of the technical solutions of the embodiments.

According to the above embodiments of the present application, a person skilled in the art may clearly understand that the embodiments of the present application may be implemented by means of hardware or by means of software plus a necessary general hardware platform. Persons of ordinary skill in the art may understand that all or part of the steps of the methods in the embodiments may be implemented by a program instructing relevant hardware. The program may be stored in a computer-readable storage medium and may be executed by at least one processor. When the program runs, the steps of the methods in the embodiments are performed. The storage medium may be any medium capable of storing program codes, such as read-only memory (ROM), a random access memory (RAM), a magnetic disk, or a compact disc-read only memory (CD-ROM).

Finally, it should be noted that the above embodiments are merely used to illustrate the technical solutions of the present application rather than limiting the technical solutions of the present application. Under the concept of the present application, the technical features of the above embodiments or other different embodiments may be combined, the steps therein may be performed in any sequence, and various variations may be derived in different aspects of the present application, which are not detailed herein for brevity of description. Although the present application is described in detail with reference to the above embodiments, persons of ordinary skill in the art should understand that they may still make modifications to the technical solutions described in the above embodiments, or make equivalent replacements to some of the technical features; however, such modifications or replacements do not cause the essence of the corresponding technical solutions to depart from the spirit and scope of the technical solutions of the embodiments of the present application.

What is claimed is:

1. A binocular brightness sensitivity measurement method based on a wearable display device, comprising:
   loading a first test image and a second test image which has a brightness different from that of the first test image respectively for two eyes of a user under test;
   acquiring an interaction instruction issued by the user under test, adjusting the brightness of the first test image and/or the second test image based on the interaction instruction until a predefined brightness sensitivity perception test condition is fulfilled;
   acquiring a brightness difference between the first test image and the second test image; and
   determining a binocular brightness sensitivity of the user under test based on the brightness difference;
   wherein the first test image is a first static image, and the second test image is a second static image; wherein image elements in the first static image or the second static image have the same brightness, the first static image has a brightness different from that of the second static image, and the brightness perception test condition is that the user under test perceives that the first static image and the second static image have the same brightness.

2. The binocular brightness sensitivity measurement method based on a wearable display device according to claim 1, further comprising: acquiring an interaction instruction issued by the user under test;
   wherein when the interaction instruction is an interaction instruction for improving the brightness of the first static image, the brightness of the first static image is increased, and the brightness of the second static image is decreased; and when the interaction instruction is an interaction instruction for improving the brightness of the second static image, the brightness of the second static image is increased, and the brightness of the first static image is decreased.

3. The binocular brightness sensitivity measurement method based on a wearable display device according to claim 1, wherein the first test image is a first dynamic image, and the second test image is a second dynamic image; wherein dynamic objects in the first dynamic image and the second dynamic image reciprocate in a plane parallel to two eyes of the user under test directly in front of the user under test, the dynamic objects in the first dynamic image and the second dynamic image have the same positions and movement trajectories, the dynamic object in the first dynamic image has a brightness different from that of the dynamic object in the second dynamic image, and the brightness perception test condition is that the movement trajectories of the dynamic objects observed by the user under test are in the same plane.

4. The binocular brightness sensitivity measurement method based on a wearable display device according to claim 3, further comprising: acquiring an interaction instruction issued by the user under test;
   wherein when the interaction instruction is an interaction instruction for improving the brightness of the first dynamic image, the brightness of the first dynamic image is increased, and the brightness of the second dynamic image is decreased; and when the interaction instruction is an interaction instruction for improving the brightness of the second dynamic image, the brightness of the second dynamic image is increased, and the brightness of the first dynamic image is decreased.

5. The binocular brightness sensitivity measurement method based on a wearable display device according to claim 1, wherein the corresponding binocular brightness sensitivity is stored to a cloud server based on a code of the user under test.

6. A mobile terminal for measuring a binocular brightness sensitivity, comprising: a head-mounted bracket, a first three-dimensional display unit and a second three-dimensional display unit; wherein the wearable display device further comprises at least one processor; wherein
   with respect to two eyes of a user under test, the first three-dimensional display unit is configured to load a first test image, and the second three-dimensional display unit is configured to load a second test image which has a brightness different from that of the first test image;
   the at least one processor is configured to acquire an interaction instruction issued by the user under test, adjust the brightness of the first test image and/or the second test image based on the interaction instruction until a predefined brightness sensitivity perception test condition is fulfilled;
   the at least one processor is configured to acquire a brightness difference between the first test image and the second test image; and
   the at least one processor is configured to determine a binocular brightness sensitivity of the user under test based on the brightness difference;
   wherein the first test image is a first static image, the second test image is a second static image; wherein image elements in the first static image or the second static image have the same brightness, the first static image has a brightness different from that of the second static image, and the brightness perception test condition is that the user under test perceives that the first static image and the second static image have the same brightness.

7. The mobile terminal for measuring a binocular brightness sensitivity according to claim 6, wherein the at least one processor is wirelessly connected to an interaction end, the interaction end being configured to collect an interaction instruction from the user under test, and wirelessly send the interaction instruction to the at least one processor; wherein when the interaction instruction is an interaction instruction for improving the brightness of the first static image, the at least one processor is further configured to increase the brightness of the first static image, and decrease the brightness of the second static image; and when the interaction instruction is an interaction instruction for improving the brightness of the second static image, the at least one processor is further configured to increase the brightness of the second static image, and decrease the brightness of the first static image.

8. The mobile terminal for measuring a binocular brightness sensitivity according to claim 6, wherein the first test image is a first dynamic image, and the second test image is a second dynamic image; wherein dynamic objects in the first dynamic image and the second dynamic image reciprocate in a plane parallel to two eyes of the user under test directly in front of the user under test, the dynamic objects in the first dynamic image and the second dynamic image have the same positions and movement trajectories, the dynamic object in the first dynamic image has a brightness different from that of the dynamic object in the second dynamic image, and the brightness perception test condition is that the movement trajectories of the dynamic objects observed by the user under test are in the same plane.

9. The mobile terminal for measuring a binocular brightness sensitivity according to claim 8, wherein the-at least one processor is wirelessly connected to an interaction end, the interaction end being configured to collect an interaction instruction from the user under test, and wirelessly send the interaction instruction to the at least one processor; wherein when the interaction instruction is an interaction instruction for improving the brightness of the first dynamic image, the brightness adjusting module is further configured to increase the brightness of the first dynamic image, and decrease the brightness of the second dynamic image; and when the interaction instruction is an interaction instruction for improving the brightness of the second dynamic image, the brightness adjusting module is further configured to increase the brightness of the second dynamic image, and decrease the brightness of the first dynamic image.

10. The mobile terminal for measuring a binocular brightness sensitivity according to claim 6, further comprising a communication module; wherein the communication module is configured to upload the measured binocular brightness sensitivity to a cloud server based on a code of the user under test.

11. A non-transitory computer-readable storage medium, the computer-readable storage medium storing computer-executable instructions, wherein the computer-executable instructions, when being executed by at least one processor, cause the at least one processor to perform the steps of:
    loading a first test image and a second test image which has a brightness different from that of the first test image respectively for two eyes of a user under test;
    acquiring an interaction instruction issued by the user under test, adjusting the brightness of the first test image and/or the second test image based on the interaction instruction until a predefined brightness sensitivity perception test condition is fulfilled;
    acquiring a brightness difference between the first test image and the second test image; and
    determining a binocular brightness sensitivity of the user under test based on the brightness difference;
    wherein the first test image is a first static image, and the second test image is a second static image; wherein image elements in the first static image or the second static image have the same brightness, the first static image has a brightness different from that of the second static image, and the brightness perception test condition is that the user under test perceives that the first static image and the second static image have the same brightness.

12. The non-transitory computer-readable storage medium according to claim 11, wherein the computer-executable instructions, when being executed by at least one processor, further cause the at least one processor to perform the steps of:
    acquiring an interaction instruction issued by the user under test;
    wherein when the interaction instruction is an interaction instruction for improving the brightness of the first static image, the brightness of the first static image is increased, and the brightness of the second static image is decreased; and when the interaction instruction is an interaction instruction for improving the brightness of the second static image, the brightness of the second static image is increased, and the brightness of the first static image is decreased.

13. The binocular brightness sensitivity measurement method based on a wearable display device according to claim 11, wherein the first test image is a first dynamic image, and the second test image is a second dynamic image; wherein dynamic objects in the first dynamic image and the second dynamic image reciprocate in a plane parallel to two eyes of the user under test directly in front of the user under test, the dynamic objects in the first dynamic image and the second dynamic image have the same positions and movement trajectories, the dynamic object in the first dynamic image has a brightness different from that of the dynamic object in the second dynamic image, and the brightness perception test condition is that the movement trajectories of the dynamic objects observed by the user under test are in the same plane.

14. The non-transitory computer-readable storage medium according to claim 13, wherein the computer-executable instructions, when being executed by at least one processor, further cause the at least one processor to perform the steps of:
    acquiring an interaction instruction issued by the user under test;
    wherein when the interaction instruction is an interaction instruction for improving the brightness of the first dynamic image, the brightness of the first dynamic image is increased, and the brightness of the second dynamic image is decreased; and when the interaction instruction is an interaction instruction for improving the brightness of the second dynamic image, the brightness of the second dynamic image is increased, and the brightness of the first dynamic image is decreased.

15. The non-transitory computer-readable storage medium according to claim 13, wherein the corresponding binocular brightness sensitivity is stored to a cloud server based on a code of the user under test.

* * * * *